(12) United States Patent
Burns et al.

(10) Patent No.: US 9,682,038 B2
(45) Date of Patent: Jun. 20, 2017

(54) PHARMACEUTICAL COMPOSITIONS COMPRISING MULTI-COMPONENT CRYSTALLINE PARTICLES SUITABLE FOR USE IN INHALATION THERAPY

(71) Applicant: Prosonix Limited, London (GB)

(72) Inventors: John Burns, Oxford (GB); Dipesh Parikh, Oxford (GB)

(73) Assignee: Prosonix Limited (GB)

(*) Notice: Subject to any disclaimer, the term of this patent is extended or adjusted under 35 U.S.C. 154(b) by 0 days.

(21) Appl. No.: 14/762,884

(22) PCT Filed: Jan. 29, 2014

(86) PCT No.: PCT/GB2014/050233
§ 371 (c)(1),
(2) Date: Jul. 23, 2015

(87) PCT Pub. No.: WO2014/118532
PCT Pub. Date: Aug. 7, 2014

(65) Prior Publication Data
US 2015/0366804 A1   Dec. 24, 2015

(30) Foreign Application Priority Data

Jan. 31, 2013 (GB) .................................. 1301723.1
Jun. 13, 2013 (GB) .................................. 1310496.3

(51) Int. Cl.
*A61K 31/137* (2006.01)
*A61K 9/00* (2006.01)
(Continued)

(52) U.S. Cl.
CPC .......... *A61K 9/0073* (2013.01); *A61K 9/0075* (2013.01); *A61K 9/16* (2013.01);
(Continued)

(58) Field of Classification Search
CPC .............. A61K 31/137; A61K 31/4015; A61K 31/4196; A61P 11/00
See application file for complete search history.

(56) References Cited

U.S. PATENT DOCUMENTS 7,754,242 B2 * 7/2010 Basu .................... A61K 9/0078
424/46
8,324,266 B2   12/2012 Vehring et al.
(Continued)

FOREIGN PATENT DOCUMENTS

EP   1894568   3/2008
GB   2447761   9/2008
(Continued)

OTHER PUBLICATIONS

International Search Report and Written Opinion for PCT/GB2014/050233 dated Mar. 3, 2014.
(Continued)

*Primary Examiner* — Carlos Azpuru
(74) *Attorney, Agent, or Firm* — Tumey L.L.P.

(57) ABSTRACT

Pharmaceutical compositions comprising multi-component crystalline particles suitable for use in inhalation therapy and for delivery by oral or nasal inhalation are provided, wherein said compositions additionally comprise particles of at least one additional active agent. Also provided are methods of preparation of the compositions and their use in medicine.

9 Claims, 5 Drawing Sheets

(51) Int. Cl.
*A61K 31/4015* (2006.01)
*A61K 31/4196* (2006.01)
*A61K 9/16* (2006.01)
*A61K 9/19* (2006.01)
*A61K 31/192* (2006.01)
*A61K 31/40* (2006.01)
*A61K 31/56* (2006.01)

(52) U.S. Cl.
CPC .............. *A61K 9/19* (2013.01); *A61K 31/137* (2013.01); *A61K 31/192* (2013.01); *A61K 31/40* (2013.01); *A61K 31/4015* (2013.01); *A61K 31/4196* (2013.01); *A61K 31/56* (2013.01)

(56) References Cited

U.S. PATENT DOCUMENTS

| 2011/0023876 | A1 | 2/2011 | Vehring et al. | |
|---|---|---|---|---|
| 2011/0146678 | A1* | 6/2011 | Ruecroft | A61K 9/0075 128/203.15 |
| 2012/0039817 | A1* | 2/2012 | Vehring | A61K 9/008 424/43 |
| 2014/0302147 | A1* | 10/2014 | Hartman | A61K 9/1617 424/489 |

FOREIGN PATENT DOCUMENTS

| WO | 03/061816 | 7/2003 |
|---|---|---|
| WO | 2007/135409 | 11/2007 |
| WO | 2008/114052 | 9/2008 |
| WO | 2010/007446 | 1/2010 |
| WO | 2010/097188 | 9/2010 |
| WO | 2010/138862 | 12/2010 |
| WO | 2010/138884 | 12/2010 |
| WO | 2011/048412 | 4/2011 |
| WO | 2012/106575 | 8/2012 |
| WO | 2012/158166 | 11/2012 |
| WO | 2013/021199 | 2/2013 |

OTHER PUBLICATIONS

Intellectual Property Office Search Report for Application No. GB1310496.3 dated Nov. 27, 2013.

Intellectual Property Office Search Report for Application No. GB1301723.1 dated May 21, 2013.

Pitchayajittipong, et al., "Engineering of crystalline combination inhalation particles of a long-acting β2-agonist and a corticosteriod" Pharmaceutical Research, vol. 26, No. 12 (2009), pp. 2657-2666.

* cited by examiner

Trace A   Trace B $(A \cup B) = A + B - 2 \times (A \cap B)$

PHARMACEUTICAL COMPOSITIONS COMPRISING MULTI-COMPONENT CRYSTALLINE PARTICLES SUITABLE FOR USE IN INHALATION THERAPY

FIELD OF THE INVENTION

The present invention relates to pharmaceutical compositions comprising multi-component crystalline particles suitable for use in inhalation therapy and for delivery by oral or nasal inhalation, wherein said compositions additionally comprise particles of at least one additional active agent. The present invention also provides methods of preparation of the compositions and their use in medicine.

BACKGROUND OF THE INVENTION

The introduction of inhalation combination products has led to significant advancements in the treatment of respiratory and pulmonary diseases and disorders. There is considerable interest in the development of the next generation of therapies with the aim of improved safety profiles and enhanced patient outcomes. One approach is to develop therapies incorporating additional therapeutic agents, for example more than one bronchodilator and an anti-inflammatory agent.

The development of inhalation combination products raises the significant pharmaceutical challenge of maintaining a controllable ratio of drug components during various stages of drug formulation and drug delivery. This challenge is especially acute with regards to the development of combination therapies involving three or more active pharmaceutical agents.

There is therefore a need to develop new pharmaceutical compositions, comprising three or more active agents, which enable the controlled delivery of active agents to the lung.

US2009/0298802 (Schering-Plough Corporation) discloses inhalable medicaments and methods based on an anti-cholinergic in combination with a corticosteroid, and a long acting beta agonist, for simultaneous or sequential administration.

WO2010/138884 (Pearl Therapeutics) provides compositions, methods and systems for pulmonary or nasal delivery of two or more active agents via a metered dose inhaler. In one embodiment, the compositions include a suspension medium, active agent particles, and suspending particles, in which the active agent particles and suspending particles form a co-suspension within the suspension medium. Example 9 describes a composition including glycopyrrolate particles, formoterol fumarate particles, mometasone furoate particles and suspending particles in HFA 134a propellant. Example 10 describes compositions including glycopyrrolate or tiotropium bromide, in combination with formoterol fumarate and mometasone furoate.

WO2012/110770 (Cipla Limited) claims pharmaceutical compositions for inhalation comprising glycopyyrolate, a beta2-agonist, and optionally an inhaled corticosteroid.

SUMMARY OF THE INVENTION

It has now been found that particularly advantageous compositions of three or more active agents for use in inhalation therapy may be prepared.

Accordingly the present invention provides a composition for inhalation therapy comprising multi-component crystalline particles and particles of at least one additional pharmacologically active ingredient, wherein the multi-component crystalline particles contain at least two pharmacologically active ingredients.

In one embodiment of the invention the particles of the at least one additional pharmacologically active ingredient are crystalline. The use of crystalline particles of active ingredients can yield benefits related to increased stability and reduced variability of the formulated composition.

In one embodiment of the invention the multi-component crystalline particles are substantially free of excipients and agents other than the active ingredients. The use of said particles could help to reduce or to eliminate the deposition and build-up of excipients upon chronic repeat dosing of a patient. This could help to reduce any associated systemic effects, for example the development of excipient intolerance or enhanced localised dissolution resulting from the presence of surfactants.

In one embodiment the invention provides a composition for the treatment of asthma, COPD or cystic fibrosis.

In a further embodiment the invention provides a composition wherein the pharmacologically active ingredients are independently selected from long-acting $\beta_2$ adrenergic receptor agonists (LABAs), anti-cholinergics including long-acting muscarinic antagonists (LAMAs), glucocorticosteroids and salts, esters, polymorphs, hydrates or solvates thereof.

In one embodiment the invention provides a composition wherein the multi-component particles comprise a LABA and a LAMA and the additional pharmacologically active ingredient is a glucocorticosteroid. In one embodiment the multi-component particles comprise glycopyrronium bromide and salmeterol xinafoate (GB-SX) and the additional pharmacologically active ingredient is fluticasone propionate. In a further embodiment the multi-component particles comprise glycopyrronium bromide and formoterol fumarate (GB-FF) and the additional pharmacologically active ingredient is fluticasone propionate. In another embodiment the multi-component particles comprise a LABA and glucocorticosteroid and the additional pharmacologically active ingredient is a LAMA.

One embodiment of the invention provides a composition wherein the multi-component particles comprise a LAMA and a glucocorticosteroid and the additional pharmacologically active ingredient is a LABA. In another embodiment, the multi-component particles comprise glycopyrronium bromide and fluticasone propionate (GB-FP) and the additional pharmacologically active ingredient is salmeterol xinafoate.

In a further embodiment the invention provides a composition wherein the multi-component particles comprise a eutectic composition. Eutectic compositions can have advantages related to the reduced thermodynamic stability of the composition leading to an increase in both equilibrium solubility and rate of dissolution of the two pharmacologically active ingredients comprising said composition.

In one embodiment the invention provides a composition deliverable from a pressurised metered dose inhaler, a dry powder inhaler or a breath activated nasal inhaler. In a further embodiment the invention provides a pharmaceutical composition deliverable from a pressurised metered dose inhaler which is substantially free of excipients and or agents other than active agents or their precursors and a pharmaceutically acceptable propellant.

In a further embodiment, the present invention provides a composition wherein the multi-component particles are prepared by a process comprising the steps:
(i) forming a solution of at least two pharmacologically active ingredients in a solvent;

(ii) subjecting the solution to a process selected from the group consisting of rapid precipitation, freeze drying, lyophilisation, rapid expansion of supercritical solutions, spray drying or mixtures thereof, wherein the said dissolved pharmacologically active ingredients are converted into a substantially dry solid material;
(iii) optionally isolating the solid material from the liquid and/or gaseous components of the process of step (ii);
(iv) treating said dry solid material from step (ii) or step (iii) with a non-solvent therefor;
(v) applying ultrasound to the solid material from step (iv) when it is in contact with said non-solvent; and
(vi) optionally separating and/or drying the resultant solid material from step (v).

Another embodiment of the invention provides a composition wherein the multi-component particles are prepared in the presence of ultrasound irradiation in a process comprising contacting a solution of at least two pharmacologically active ingredients in a first flowing stream with an antisolvent in a second flowing stream, causing the mixing thereof, and collecting the crystalline particles that are generated.

Another aspect of the invention provides a dry powder inhaler, a pressurised metered dose inhaler or a breath activated nasal inhaler containing a composition according to the invention.

In a further aspect, the present invention provides a method of treating a respiratory disease or disorder or a pulmonary disease or disorder in a patient using compositions or inhalers according to the invention.

In another aspect the invention provides compositions or inhalers according to the invention for use in the treatment of a respiratory disease or disorder or a pulmonary disease or disorder.

In another aspect the invention provides compositions or inhalers and uses thereof substantially as described herein and with reference to the accompanying examples.

A particular advantage of the current invention is the ability to optimise the delivery of multiple active agents to the lung. The optimisation can involve a targeted delivery of the active agents to specific regions of the lung.

The current invention therefore has the potential to enhance the effect at the molecular and cellular level through synergistic pharmacological mechanisms, with the consequence of achieving acceptable efficacy at a reduced dose and an improved risk-benefit profile.

An example of this optimisation is in the consistent localised delivery of a specified ratio of active ingredients. An enhanced co-location can result from the combination of two or more actives into a multi-component particle, and may also result from interactions between the multi-component particles and the particles of an additional active ingredient. Enhanced co-location may yield an increased likelihood of synergistic effects.

The interaction between the multi-component particles and particles of an additional active ingredient may also be reduced when compared to the particles of the individual components. This could therefore lead to an alternative distribution of active ingredients within the lung when using a composition of the current invention when compared to that of a blend of three individual components.

The compositions of the invention therefore offer the opportunity to fine tune the delivery of multiple active agents to the lung, enhancing or reducing co-location of active ingredients by design. This may be achieved, for example, by selecting which active pharmaceutical ingredients (APIs) are included in the multi-component particles, or the ratio of APIs within the multi-component particles, leading to alternative particle surface characteristics and increasing or reducing cohesion between particles and therefore blend interactions. Modifying the lung distribution of active ingredients within a combination therapy may yield therapeutic benefits, for example an improved risk-benefit profile.

The co-location of active ingredients delivered using a composition of the current invention may be compared to a blend of particles of individual active ingredients using an Anderson Cascade Impactor (ACI). The ACI traces can be converted to represent the proportion of each API at each stage compared to the total delivered. A single number representation of how well two traces match can be calculated as the ratio of the area of intersection of the two traces divided by the area of the union of the two traces (see FIG. 1). For identical traces this will take a value of 1, and for traces with no overlap it will take the value of zero. Mathematically it is represented as, Co-Location Performance(%)=Area of($(A \cap B)$)/Area of($(A \cup B)$))*100.

The ACI traces may also be analysed to determine the co-location of APIs using the following calculation:

Co-location=(sum across $z$ stages(minimum % deposition of any active on stage $z$)/sum across $z$ stages(maximum % deposition of any active on stage $z$))*100

The value from this analysis will be 100% if perfectly co-located and 0% if the APIs land on completely different stages. Compositions of the current invention may have a co-location of APIs, as determined by ACI analysis, of greater than 70%, for example greater than 75% or greater than 80%.

A further benefit of the invention is in regards to the dissolution rates of active ingredients within the pharmaceutical composition. Incorporation of active ingredients into a multi-component particle can lead to a linked release of different components and therefore a more rapid onset of action of one or more actives. These effects have the potential to increase the likelihood of synergistic action of two or more actives with different dissolution rates.

In addition, actives within a multi-component particle may comprise a eutectic composition, whereby the melting temperature is lower than that of either pure compound. A eutectic composition may behave differently with respect to melting point, solubility and chemical stability.

In one embodiment of the invention, the pharmaceutical composition comprises multi-component particles comprising glycopyrronium bromide and salmeterol xinafoate (GB-SX), glycopyrronium bromide and formoterol fumarate (GB-FF), tiotropium bromide and salmeterol xinafoate (TIO-SX) or tiotropium bromide and formoterol fumarate (TIO-FF) and wherein the composition further comprises particles of a glucocorticosteroid selected from the group consisting of fluticasone, budesonide, mometasone or ciclesonide.

In a further embodiment of the invention, the pharmaceutical composition comprises multi-component particles comprising fluticasone propionate and salmeterol xinafoate (FP-SX) or budesonide and formoterol fumarate (BDS-FF) and wherein the composition further comprises particles of a long-acting muscarinic antagonist (LAMA) selected from glycopyrronium or tiotropium.

In a another embodiment of the invention, the pharmaceutical composition comprises multi-component particles comprising fluticasone propionate and glycopyrronium bromide (FP-GB) or budesonide and glycopyrronium bromide (BDS-GB) and wherein the composition further comprises particles of a long-acting $\beta_2$ adrenergic receptor agonist (LABA) selected from salmeterol or formoterol.

DETAILED DESCRIPTION OF THE INVENTION

The present invention provides pharmaceutical compositions comprising multi-component particles (MCPs) and particles of at least one additional active agent. Multi-component particles of the invention comprise at least two pharmacologically active ingredients or precursors thereof. The two pharmacologically active ingredients may be selected from different classes of agents. The two pharmacologically active ingredients may be selected from the same class of agents.

Multi-component particles according to the current invention are crystalline and, when analysed by differential scanning calorimetry (DSC), show no significant exotherm which would indicate to the skilled person the presence of amorphous material. It will be appreciated that crystalline particles of the invention may comprise minor regions of amorphous material. By minor regions it is meant that the crystalline particles are less than 5% amorphous, preferably less than 1% amorphous.

Multi-component crystalline particles of the invention may be substantially free of excipients and agents other than active agents or their precursors. By substantially free it is meant that the crystalline particles contain less than 10% by weight of excipients and agents other than active agents of their precursors, more preferably less than 5%, more preferably less than 2%.

Multi-component particles and particles of additional active agents of the current invention may, for example, comprise active agents selected from $\beta_2$ adrenergic receptor agonists, anti-cholinergics including muscarinic antagonists, glucocorticosteroids, methylxanthine compounds, anti-histamines, decongestants, anti-tussive drug substances, PDEI-VI inhibitors or calcium blockers.

Preferably, active agents are selected from $\beta_2$ adrenergic receptor agonists, anti-cholinergics including muscarinic antagonists and glucocorticosteroids. Long-acting $\beta_2$ adrenergic receptor agonists (LABAs) and long-acting muscarinic antagonists (LAMAs) have a prolonged duration of action, such as greater than 12 hours, and are therefore suitable for once- or twice-daily dosing.

Preferred $\beta_2$ adrenergic receptor agonists are LABAs, preferably selected from the group consisting of formoterol, salmeterol, carmoterol, indacaterol, vilanterol, arformoterol, bambuterol, isoproterenol, milveterol, clenbuterol, olodaterol and salts, esters, polymorphs, hydrates, solvates or isomers thereof. A particularly preferred salt of formoterol is formoterol fumarate (FF). A particularly preferred salt of salmeterol is salmeterol xinafoate (SX). $\beta_2$ agonists may also be short acting $\beta_2$ agonists such as fenoterol, salbutamol, levalbuterol, procaterol, terbutaline, pirbuterol, procaterol, metaproterenol, bitolterol, ritodrine, albuterol and salts, esters, polymorphs, hydrates, solvates or isomers thereof, preferably fenoterol hydrobromide.

Formoterol fumarate of the current invention may be in an anhydrous form or present as a hydrate, for example as a monohydrate or dihydrate. Compositions of the current invention may comprise racemic formoterol, one of the enantiomers, one of the diastereomers or a mixture thereof.

Preferred anti-cholinergics are LAMAs preferably selected from the group consisting of glycopyrronium, tiotropium, aclidinium, darotropium, umedlidinium and salts, esters, polymorphs, hydrates, solvates or isomers thereof. A preferred short-acting muscarinic antagonist is ipratropium and salts, esters, polymorphs, hydrates or solvates thereof. Particularly preferred muscarinic antagonist are selected from the group consisting of glycopyrronium bromide, tiotropium bromide, ipratropium bromide, aclidinium bromide, darotropium bromide or umeclidinium bromide and salts, esters, polymorphs, hydrates, solvates or isomers thereof.

Preferred glucocorticosteroids are selected from the group consisting of mometasone, beclamethasone, budesonide, fluticasone, ciclesonide or triamcinolone and salts, esters, polymorphs, hydrates, solvates or isomers thereof, preferably beclamethasone dipropionate, fluticasone propionate, fluticasone furoate, mometasone furoate, or budesonide.

Preferred multi-component particles of the current invention comprise glycopyrronium bromide and salmeterol xinafoate (GB-SX), glycopyrronium bromide and formoterol fumarate (GB-FF), tiotropium bromide and salmeterol xinafoate (TIO-SX), tiotropium bromide and formoterol fumarate (TIO-FF), fluticasone propionate and salmeterol xinafoate (FP-SX), budesonide and formoterol fumarate (BDS-FF), fluticasone propionate and glycopyrronium bromide (FP-GB) or budesonide and glycopyrronium bromide (BDS-GB). Particularly preferred multi-component particles comprise glycopyrronium bromide and salmeterol xinafoate (GB-SX), fluticasone propionate and glycopyrronium bromide (FP-GB) and glycopyrronium bromide and formoterol fumarate (GB-FF).

The multi-component particles may have a molar ratio of 100:1 to 1:1, 50:1 to 1:1, 10:1 to 1:1, 9:1 to 1:1, 4:1 to 1:1 or 2:1 to 1:1. Alternatively, the multi-component particles may have a mass ratio of 100:1 to 1:1, 50:1 to 1:1, 10:1 to 1:1, 9:1 to 1:1, 4:1 to 1:1, 2:1 to 1:1.

Suitable multi-component particles include particles with a LAMA to LABA mass ratio of 100:1, 50:1, 20:1, 17:1, 10:1, 8:1, 7.5:1, 4:1, 2:1, 1.5:1, 1:1, 1:2, 1:2.5 or 1:4, multi-component particles with a LAMA to glucocorticosteroid mass ratio of 1:1, 1:2, 1:8 or 1:20, or multi-component particles with a LABA to glucocorticosteroid mass ratio of 2:1, 1:1, 1:2, 1:4, 1:8, 1:10, 1:17, 1:20, 1:33, 1:40 or 1:80.

Multi-component particles of the current invention may comprise a eutectic composition. A eutectic composition has a lower melting point than that of either pure compound. A eutectic composition is clearly differentiated from the phenomenon of co-crystal formation. A person skilled in the art will appreciate that in a eutectic composition the two constituent materials are independently crystalline whereas in the case of a co-crystal a completely new crystalline phase forms and in effect replaces the separate crystalline phases with respect to the component molecules within each unit cell.

In order to determine whether or not a eutectic composition exists or can be found, a person skilled in the art could use differential scanning calorimetry (DCS) to verify the melting point and the magnitude of melting point suppression. The particles comprising a eutectic composition may further comprise an excess of at least one of the pharmacologically active ingredients.

A suitable eutectic composition is a LABA and LAMA at a 1:1 molar ratio, such as glycopyrronium bromide and salmeterol xinafoate at a 1:1 molar ratio.

Compositions of the invention comprise particles with a size distribution suitable for oral or nasal inhalation, for example with a mean mass aerodynamic diameter of up to 10 μm, up to 5 μm or up to 1 μm (for example as determined by ACI analysis).

Multi-component particles may be prepared using the UMAX (Ultrasound Mediated Amorphous to Crystalline transition) method as described in WO2010/007447. In an alternative process, the multi-component particles are prepared using equipment as described in WO 2008/114052. The particles are prepared in the presence of ultrasonic irradiation in a process comprising contacting a solution in a first flowing stream with an anti-solvent in a second flowing stream, causing the mixing thereof, and collecting crystalline particles that are generated.

Compositions of the invention comprise multi-component particles and particles of at least one additional pharmacologically active ingredient. Preferred compositions comprise multi-component particles selected from the group GB-SX, GB-FF, TIO-SX and TIO-FF combined with particles selected from the group fluticasone propionate (FP), budesonide, mometasone or ciclesonide. Further preferred compositions comprise multi-component particles selected from FP-SX and BDS-FF combined with particles selected from glycopyrronium and tiotropium. Other preferred compositions comprise multi-component particles selected from FP-GB and BDS-GB combined with particles selected from salmeterol xinafoate and formoterol fumarate.

In one embodiment of the invention the compositions are suitable for administration by a pressurised metered dose inhaler (pMDI). Such compositions comprise a pharmaceutically acceptable propellant. Suitable propellants may be selected from the group of HFA propellants, for example HFA134a (1,1,1,2-tetrafluoroethane) or HFA 227 (1,1,1,2,3,3,3,-heptafluoropropane).

Compositions of the current invention suitable for pMDI may be substantially free of excipients and or agents other than active agents or their precursors and the pharmaceutically acceptable propellant. By substantially free it is meant that the composition contain less than 10% by weight of excipients and agents other than active agents or their precursors and a pharmaceutically acceptable propellant.

In one embodiment of the current invention the composition comprises multi-component particles comprising a LABA and a LAMA and glucocorticosteroid particles as a suspension in HFA propellant. In another embodiment of the invention the composition comprises multi-component particles comprising glycopyrrolate and salmeterol, and fluticasone particles as a suspension in HFA propellant. In a further embodiment of the invention the composition comprises multi-component particles comprising glycopyrrolate and formoterol, and fluticasone particles as a suspension in HFA propellant. In another embodiment of the invention the aforementioned compositions are substantially free of excipients and or agents other than active agents or their precursors and the pharmaceutically acceptable propellant. In a further embodiment the fluticasone particles are crystalline.

In another embodiment of the invention the compositions are suitable for administration by a dry powder inhaler (DPI). Such compositions comprise a suitable carrier, for example a sugar, such as lactose. Compositions for administration by a DPI may additionally comprise a surface agent, for example magnesium stearate.

Methods of formulating compositions and pharmaceutically acceptable propellants, carriers and surface agents are known to one skilled in the art, for example by reference to texts such as Respiratory Drug Delivery: Essential Theory & Practice by Stephen Newman (Respiratory Drug Delivery Online, 2009).

The pharmaceutical compositions of the present invention can be administered by a dry powder inhaler, a pressurised metered dose inhaler, or a breath activated nasal inhaler. The invention therefore provides a dry powder inhaler, a pressurized metered-dose inhaler or a breath activated nasal inhaler comprising a composition of the invention.

The invention will now be described in more detail with reference to and by way of examples which are intended to be illustrative only. It is to be understood that the examples and figures are not to be construed as limiting the scope of the invention in any way.

EXAMPLES

Example 1

Glycopyrronium Bromide:Salmeterol Xinafoate (GB:SX) Multi-component Particles (2:1 Mass Ratio) in Combination with Fluticasone Propionate Crystalline particles of fluticasone propionate suitable for inhalation may be prepared using methods known in the art, for example as described in WO2010/007446A1.

The GB:SX multi-component particles (MCPs) can be prepared, for example, using conventional equipment as described in WO 2008/114052. Particles have been prepared using the following methodology:

A solution of GB/SX (mass ratio 2:1) in methanol was prepared at room temperature. The solution was added to a re-circulating stream of di-isopropyl ether (DIPE) in the presence of 40 W ultrasound power using a thick probe based system. The material was isolated by filtration. The following parameters were used:

Solution concentration: 25% (6.8 g in 27 ml methanol)
Volume DIPE: 648 ml
Solution-non-solvent ratio: 1/24 V/V
Reaction vessel temperature: 7.4+/−0.2° C.
Solution addition rate: 0.5 ml/min
Solution addition velocity: 0.042 m/s
Solution addition tube diameter: 0.5 mm
Duration of addition: 60 mins
Re-circulation rate: 2.63 L/min Velocity of re-circulating anti-solvent stream: 0.9 m/s at entry to ultrasonic cell
Flow rate ratio: 5260:1
Ultrasound: 40 W
Moisture content in the processed slurry (by Karl Fischer titration): 0.015%

The following composition has been prepared by loading the particles in the desired ratio into HFA134a and homogenising (micrograms (mcg), q.s. meaning a sufficient quantity):

| Ingredient | Quantity/spray |
| --- | --- |
| MCP - Glycopyrronium bromide:Salmeterol xinafoate (2:1 by mass) | 50:25 mcg |
| Fluticasone propionate | 50 mcg |
| HFA134a | q.s. |

Figure 5:
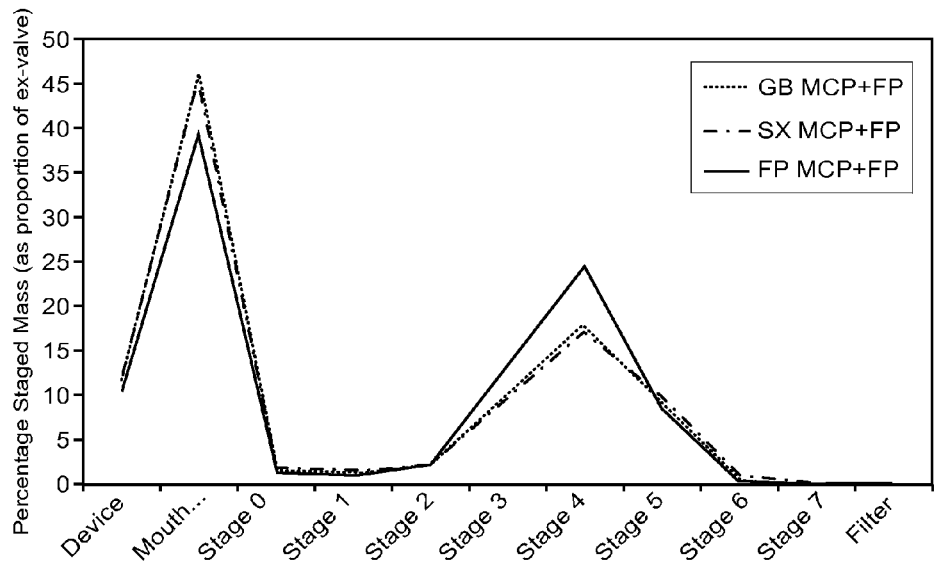
FIG. 5 shows the ACI trace of a GB-SX MCP and FP triple combination formulation
Figure 6:
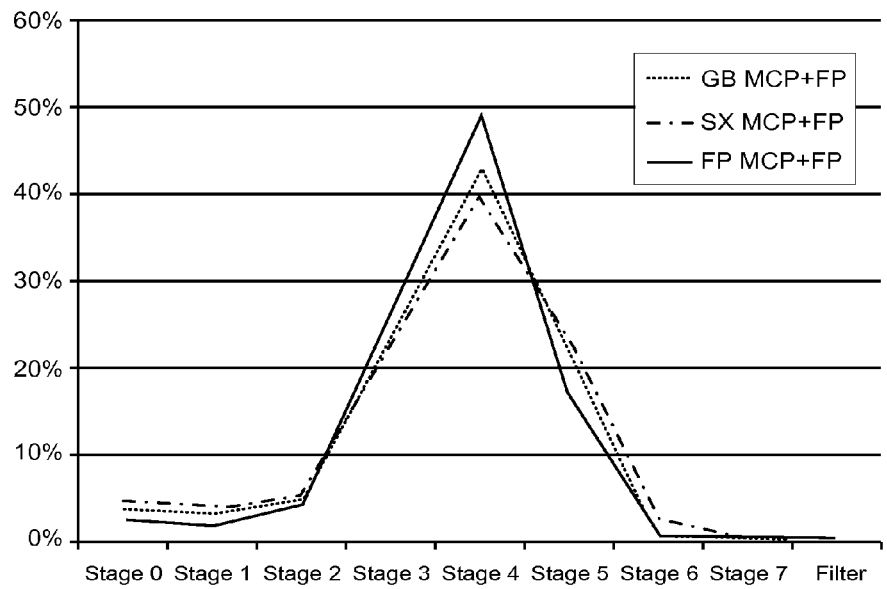
FIG. 6 shows the percentage of each API at each stage (device and mouth stages removed from the analysis) for the GB-SX MCP and FP triple combination.

The composition was analysed using an Anderson Cascade Impactor (ACI) (FIG. 5). The traces were analysed to determine % deposition of each active at each stage excluding the device and mouth stages (FIG. 6). The co-location of the three APIs was then analysed using the formula:

Co-location=(sum across $z$ stages(minimum % deposition of any active on stage $z$)/sum across $z$ stages(maximum % deposition of any active on stage $z$))*100

The co-location figure generated was compared to an analysis of the overlaid ACI traces of the single formulations (FIG. 2) and an ACI trace of a blended formulation of the three APIs (FIG. 3):

| Formulation | Co-location |
| --- | --- |
| GB, FP, SX single formulations overlaid | 31% |
| GB, FP, SX blended formulation | 61% |
| GB-SX MCP blended with FP (Ex. 1) | 78% |

Figure 1:
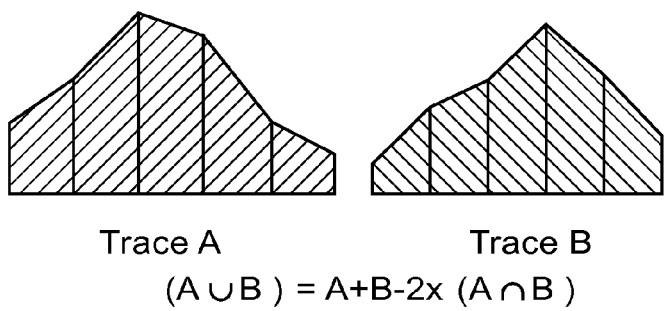
FIG. 1 shows a schematic of the method of quantification of co-location performance.
Figure 1:
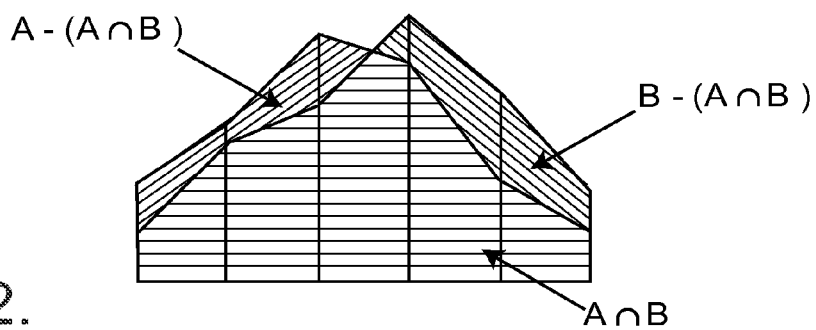
Figure 2:
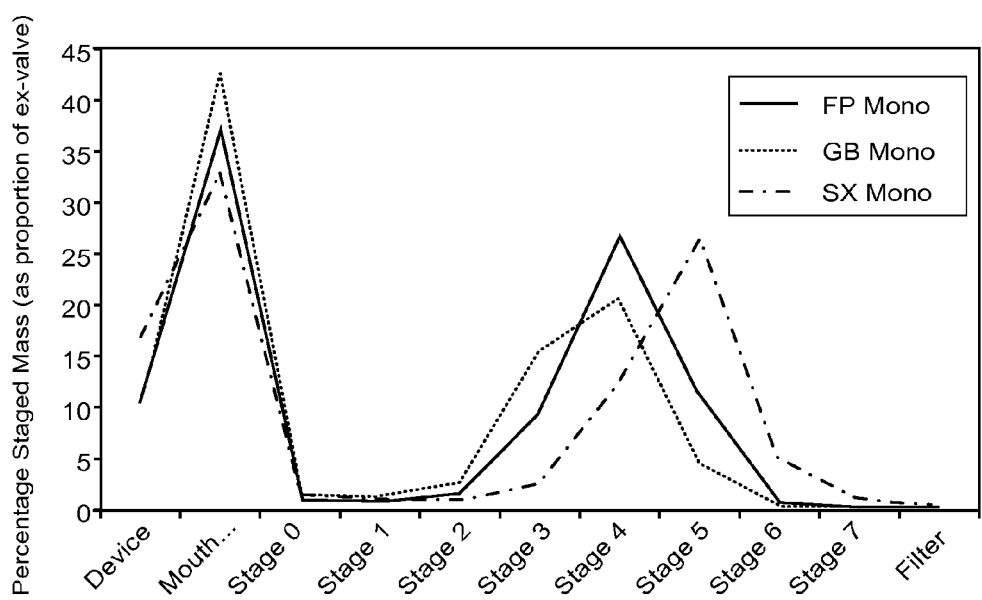
FIG. 2 shows overlaid ACI traces of FP, SX and GB mono formulations.
Figure 3:
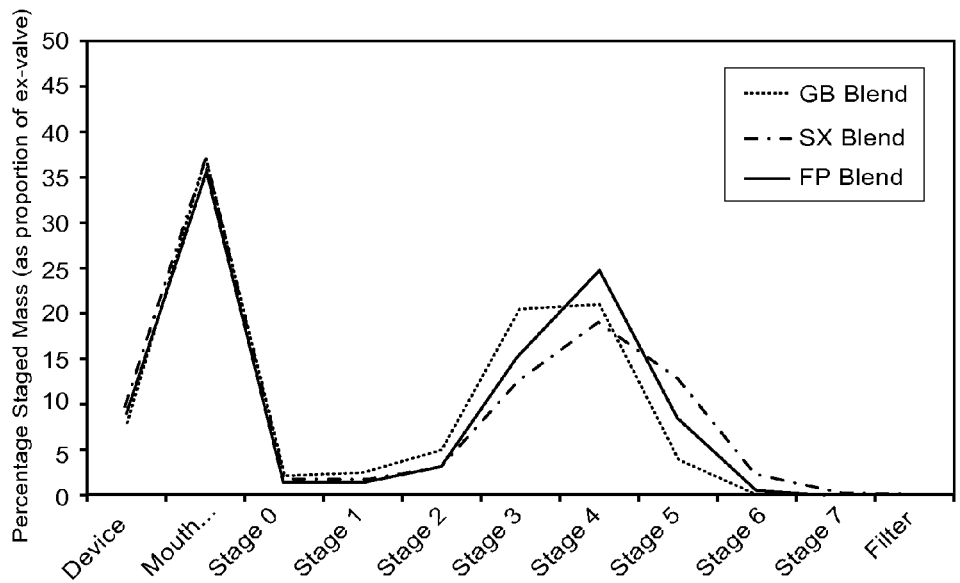
FIG. 3 shows the ACI trace of an FP, SX and GB triple blended formulation.

A comparison of the data shown in FIG. 2 (overlaid mono-formulations) and FIG. 3 (triple blended formulations) shows that blend interactions are occurring between FP and SX which leads to improved co-location of these APIs.

Figure 4:
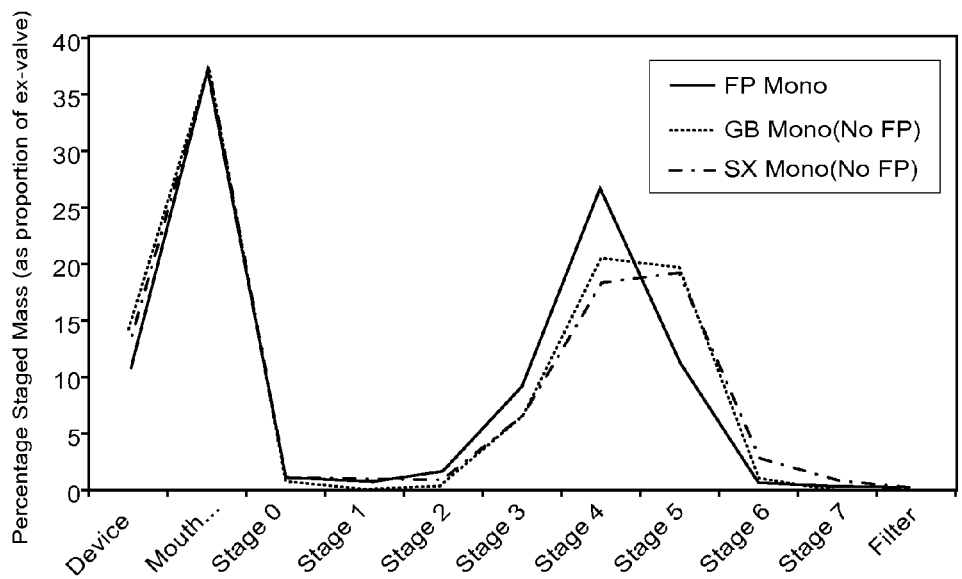
FIG. 4 shows the overlaid ACI traces of a GB-SX MCP formulation and an FP formulation.

A comparison of the data shown in FIG. 4 (overlaid GB-SX MCP formulation and an FP mono-formulation) and FIG. 5 (GB-SX MCP and FP triple formulation) indicates that an unexpectedly strong blend interaction occurs between GB-SX multi-component particles and FP particles which leads to enhanced co-location of all three APIs in the triple formulation.

Example 2

Glycopyrronium Bromide:Salmeterol Xinafoate (GB:SX) Multi-component Particles (1:1 Ratio) in Combination with Fluticasone Propionate Crystalline particles of fluticasone propionate suitable for inhalation may be prepared using methods known in the art, for example as described in WO2010/007446A1.

The GB:SX multi-component particles can be prepared, for example, using conventional equipment as described in WO 2008/114052. Particles have been prepared using the following methodology:

A solution of GB/SX (ratio 1:1) in methanol was prepared at room temperature. The solution was added to a re-circulating stream of di-isopropyl ether (DIPE) in the presence of 39 W ultrasound power using a thick probe based system. The material was isolated by filtration. The following parameters were used:

Temperature=6 deg C
Methanol/DIPE (W/V)=20%
Re-circulation rate=2.4 L/min
Velocity of re-circulating anti-solvent stream at entry to ultrasonic cell=0.8 m/s
Moisture content=0.02%
Addition rate=0.5 mL/min
Addition tube diameter=0.5 mm
Flow Cell=Syrris SL10

The following compositions may be prepared by loading the particles in the desired ratio into HFA134a and homogenising:

Example 2a

| Ingredient | Quantity/spray |
| --- | --- |
| MCP - Glycopyrronium bromide:Salmeterol xinafoate (1:1 by mass) | 25:25 mcg |
| Fluticasone propionate | 50 mcg |
| HFA134a | q.s. |

Example 2b

| Ingredient | Quantity/spray |
| --- | --- |
| MCP - Glycopyrronium bromide:Salmeterol xinafoate (1:1 by mass) | 25:25 mcg |
| Fluticasone propionate | 125 mcg |
| HFA134a | q.s. |

Example 2c

| Ingredient | Quantity/spray |
| --- | --- |
| MCP - Glycopyrronium bromide:Salmeterol xinafoate (1:1 by mass) | 25:25 mcg |
| Fluticasone propionate | 250 mcg |
| HFA134a | q.s. |

The following compositions may be prepared by blending:

Example 2d

| Ingredient | Quantity/unit |
| --- | --- |
| MCP - Glycopyrronium bromide:Salmeterol xinafoate (1:1 by mass) | 25:25 mcg |
| Fluticasone propionate | 50 mcg |
| Lactose | 12.4 mg |

Example 2e

| Ingredient | Quantity/unit |
|---|---|
| MCP - Glycopyrronium bromide:Salmeterol xinafoate (1:1 by mass) | 25:25 mcg |
| Fluticasone propionate | 125 mcg |
| Lactose | 12.325 mg |

Example 2f

| Ingredient | Quantity/unit |
|---|---|
| MCP - Glycopyrronium bromide:Salmeterol xinafoate (1:1 by mass) | 25:25 mcg |
| Fluticasone propionate | 250 mcg |
| Lactose | 12.2 mg |

Example 3

Glycopyrronium Bromide:Formoterol Fumarate (GB:FF) Multi-component Particles (4:1 Mass Ratio) in Combination with Fluticasone Propionate Crystalline particles of fluticasone propionate suitable for inhalation may be prepared using methods known in the art, for example as described in WO2010/007446A1.

The GB:FF multi-component particles can be prepared, for example, using conventional equipment as described in WO 2008/114052. The particles have been prepared using the following methodology:

A solution of GB/FF (mass ratio 3.75:1) in methanol was prepared at room temperature. The solution was added to a re-circulating stream of tert-butylmethyl ether (TBME) in the presence of 39 W ultrasound power using a thick probe based system. The material was isolated by filtration. The following parameters were used:

Temperature=7 deg C
Methanol/TBME (W/W)=25%
Re-circulation rate=2.6 L/min
Velocity of re-circulating anti-solvent stream at entry to ultrasonic cell=0.9 m/s
Moisture content=0.04%
Addition rate=0.5 mL/min
Addition tube diameter=0.5 mm
Flow cell=Syrris SL10

The following compositions may be prepared by loading the particles in the desired ratio into HFA134a and homogenising:

Example 3a

| Ingredient | Quantity/spray |
|---|---|
| MCP - Glycopyrronium bromide:formoterol fumarate (4:1 by mass) | 24:6 mcg |
| Fluticasone propionate | 50 mcg |
| HFA134a | q.s. |

Example 3b

| Ingredient | Quantity/spray |
|---|---|
| MCP - Glycopyrronium bromide:formoterol fumarate (4:1 by mass) | 24:6 mcg |
| Fluticasone propionate | 125 mcg |
| HFA134a | q.s. |

Example 3c

| Ingredient | Quantity/spray |
|---|---|
| MCP - Glycopyrronium bromide:formoterol fumarate (4:1 by mass) | 24:6 mcg |
| Fluticasone propionate | 250 mcg |
| HFA134a | q.s. |

The following compositions may be prepared by blending:

Example 3d

| Ingredient | Quantity/unit |
|---|---|
| MCP - Glycopyrronium bromide:formoterol fumarate (4:1 by mass) | 24:6 mcg |
| Fluticasone propionate | 50 mcg |
| Lactose | 12.42 mg |

Example 3e

| Ingredient | Quantity/unit |
|---|---|
| MCP - Glycopyrronium bromide:formoterol fumarate (4:1 by mass) | 24:6 mcg |
| Fluticasone propionate | 125 mcg |
| Lactose | 12.345 mg |

Example 3f

| Ingredient | Quantity/unit |
|---|---|
| MCP - Glycopyrronium bromide:formoterol fumarate (4:1 by mass) | 24:6 mcg |
| Fluticasone propionate | 250 mcg |
| Lactose | 12.22 mg |

The following compositions have been prepared by loading the particles in the desired ratio into HFA134a and homogenising:

Example 3g

| Ingredient | Quantity/unit |
| --- | --- |
| MCP - Glycopyrronium bromide:formoterol fumarate (4:1 by mass) | 36:9 mcg |
| Fluticasone propionate | 50 mcg |
| HFA134a | q.s. |

Example 3h

| Ingredient | Quantity/unit |
| --- | --- |
| MCP - Glycopyrronium bromide:formoterol fumarate (4:1 by mass) | 36:9 mcg |
| Fluticasone propionate | 125 mcg |
| HFA134a | q.s. |

Example 3i

| Ingredient | Quantity/unit |
| --- | --- |
| MCP - Glycopyrronium bromide:formoterol fumarate (4:1 by mass) | 36:9 mcg |
| Fluticasone propionate | 250 mcg |
| HFA134a | q.s. |

Figure 7:
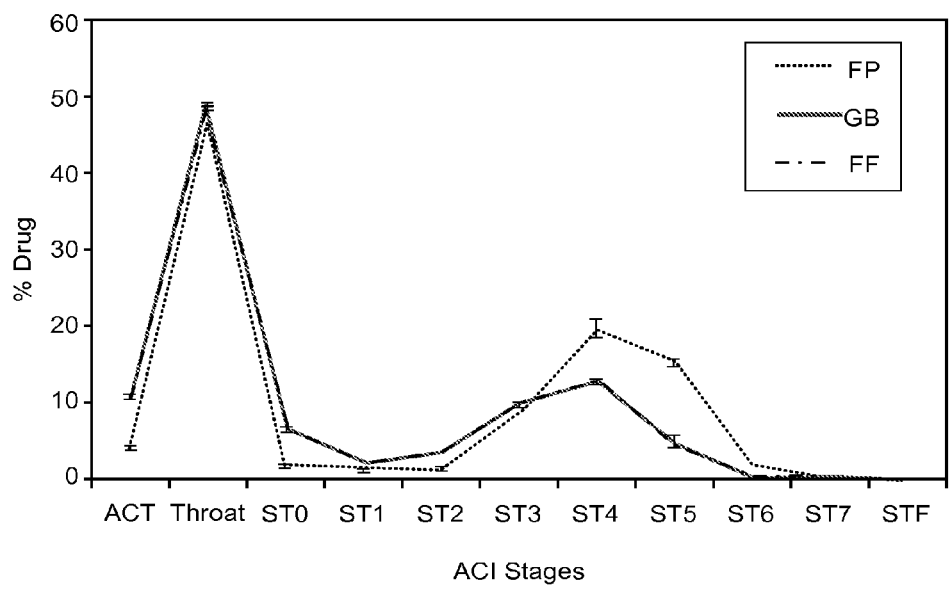
FIG. 7 shows the ACI trace of a GB-FF MCP and FP triple combination formulation as described in Example 3g.
Figure 8:
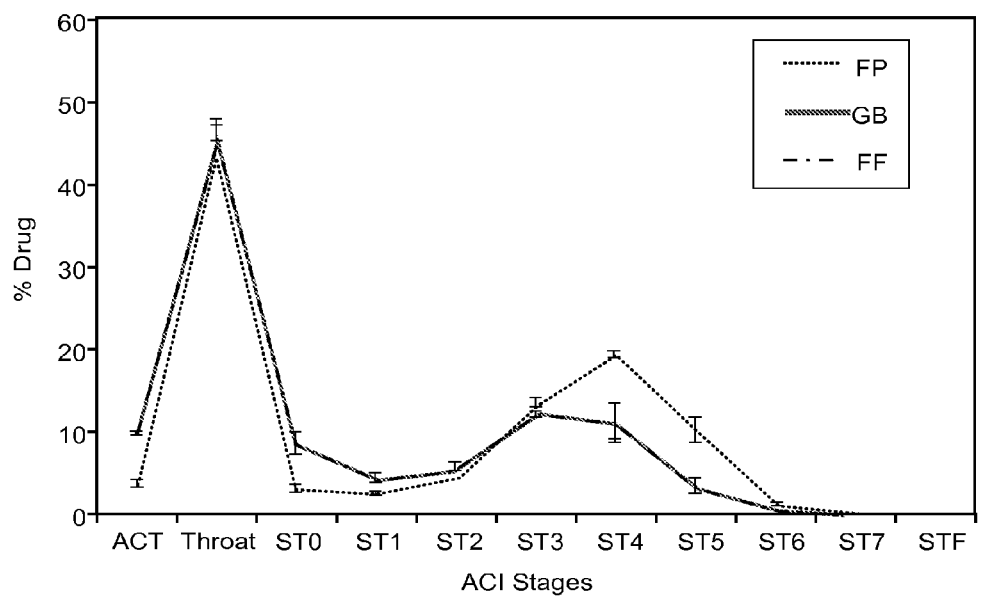
FIG. 8 shows the ACI trace of a GB-FF MCP and FP triple combination formulation as described in Example 3h.
Figure 9:
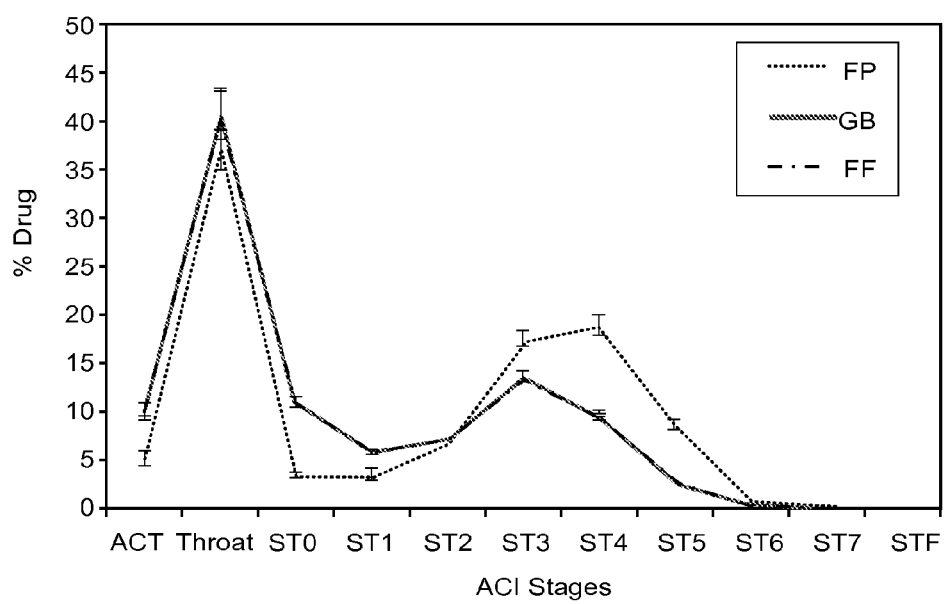
FIG. 9 shows the ACI trace of a GB-FF MCP and FP triple combination formulation as described in Example 3i.

The compositions detailed in example 3g, 3h and 3i were analysed using an Anderson Cascade Impactor (ACI). The data is shown in FIGS. 7-9. This data shows a high level of co-location between the multi-component particle components (GB and FF), however a lower level of co-location with FP. The ACI data indicates that a low blend interaction occurs between the FP particles and the GB-FF MCPs.leading to an alternative distribution of LABA and glucocorticosteroid active agents than could be achieved using a blended formulation (see for example FIG. 3).

Example 4

Fluticasone Propionate:Glycopyrronium Bromide (FP:GB) Multi-component Particles (10:1 Mass Ratio) in Combination with Salmeterol Xinafoate Crystalline particles of salmeterol xinafoate suitable for inhalation may be prepared using methods known in the art, for example as described in WO 2008/114052.

The FP:GB multi-component particles may be prepared using, for example, the methodology described in WO2010/007447A1 (UMAX processing). The particles have been prepared by UMAX processing using the following parameters:

1 g of spray dried combination particles (amorphous material) was dispersed in 100 mL of PP1-Perfluoro-2-methylpentane (1 g/100 mL).
Temperature=40 deg C
Ultrasound power=15 W
Batch process (under pressure) 2 bar
Sonication period 4 hrs.

The following compositions may be prepared by loading the particles in the desired ratio into HFA134a and homogenising:

Example 4a

| Ingredient | Quantity/spray |
| --- | --- |
| MCP - Fluticasone Propionate:Glycopyrronium bromide (10:1 by mass) | 250:25 mcg |
| Salmeterol Xinafoate | 25 mcg |
| HFA134a | q.s. |

The following compositions may be prepared by blending:

Example 4b

| Ingredient | Quantity/unit |
| --- | --- |
| MCP - Fluticasone Propionate:Glycopyrronium bromide (10:1 by mass) | 250:25 mcg |
| Formoterol fumarate | 25 mcg |
| Lactose | 12.2 mg |

What is claimed:

1. A composition for inhalation therapy comprising multi-component crystalline particles and also particles of fluticasone propionate, wherein the multi-component crystalline particles comprise glycopyrronium bromide and salmeterol xinafoate (GB-SX) as active ingredients and are substantially free of excipients and substances other than the active ingredients.

2. A composition according to claim 1 wherein the particles of fluticasone propionate are crystalline.

3. A composition according to claim 1 for the treatment of asthma, COPD or cystic fibrosis.

4. A composition according to claim 1 wherein the multi-component particles comprise a eutectic composition.

5. A composition according to claim 1 deliverable from a pressurised metered dose inhaler, a dry powder inhaler or a breath activated nasal inhaler.

6. A composition deliverable from a pressurised metered dose inhaler according to claim 5 which is substantially free of excipients and substances other than the active agents and a pharmaceutically acceptable propellant.

7. A composition according to claim 1 wherein the multi-component particles are prepared by a process comprising the steps:
   (i) forming a solution of glycopyrronium bromide and salmeterol xinafoate in a solvent;
   (ii) subjecting the solution to a process selected from the group consisting of rapid precipitation, freeze drying, lyophilisation, rapid expansion of supercritical solutions, spray drying or mixtures thereof, wherein the glycopyrronium bromide and salmeterol xinafoate are converted into a substantially dry solid material;
   (iii) optionally isolating the solid material from the liquid and/or gaseous components of the process of step (ii);
   (iv) treating said dry solid material from step (ii) or step (iii) with a non-solvent therefor;
   (v) applying ultrasound to the solid material from step (iv) when it is in contact with said non-solvent; and
   (vi) separating and/or drying the resultant solid material from step (v).

8. A composition according to claim 1 wherein the multi-component particles are prepared in the presence of ultrasound irradiation in a process comprising contacting a solution of glycopyrronium bromide and salmeterol xinafoate in a first flowing stream with an anti-solvent in a second flowing stream, causing the mixing thereof, and collecting the crystalline particles that are generated.

9. A composition according to claim 1 for treatment of a respiratory disease or disorder or a pulmonary disease or disorder.

* * * * *